United States Patent [19]

Dahlstrand

[11] Patent Number: 5,462,050
[45] Date of Patent: Oct. 31, 1995

[54] ANESTHETIC MASK FOR INFANTS

[75] Inventor: Monika Dahlstrand, Karlskrona, Sweden

[73] Assignee: Engstrom Medical Aktiebolag, Sweden

[21] Appl. No.: 178,239

[22] PCT Filed: Jun. 25, 1992

[86] PCT No.: PCT/SE92/00470

§ 371 Date: Jan. 10, 1994

§ 102(e) Date: Jan. 10, 1994

[87] PCT Pub. No.: WO93/01854

PCT Pub. Date: Feb. 4, 1993

[30] Foreign Application Priority Data

Jul. 19, 1991 [SE] Sweden ................ 9102205

[51] Int. Cl.⁶ .................. A61M 16/01
[52] U.S. Cl. .............. 128/207.18; 128/206.29; 128/205.25
[58] Field of Search .......... 128/207.18, 200.26, 128/201.26, 205.25, 206.29

[56] References Cited

U.S. PATENT DOCUMENTS

| | | | |
|---|---|---|---|
| 2,012,441 | 8/1935 | Willson et al. ............... | 128/205.25 |
| 3,037,501 | 6/1962 | Miller ........................... | 128/206.29 |
| 3,091,236 | 5/1963 | Delbert ......................... | 128/206.29 |
| 3,426,755 | 2/1969 | Clegg ............................ | 128/206.29 |
| 4,520,809 | 6/1985 | de Greef et al. . | |
| 4,669,461 | 6/1987 | Battaglia et al. ............ | 128/202.13 |
| 4,706,683 | 11/1987 | Chilton et al. ............... | 128/205.25 |
| 4,896,666 | 1/1990 | Hinkle . | |

FOREIGN PATENT DOCUMENTS

| | | | |
|---|---|---|---|
| 720046 | 3/1942 | Germany .................. | 128/205.25 |
| 1437033 | 7/1986 | U.S.S.R. .................... | 128/205.25 |
| 2081105 | 2/1982 | United Kingdom ....... | 128/206.29 |
| 2231497 | 11/1990 | United Kingdom ....... | 128/206.29 |

Primary Examiner—Edgar S. Burr
Assistant Examiner—William J. Deane, Jr.
Attorney, Agent, or Firm—Lerner, David, Littenberg, Krumholz & Mentlik

[57] ABSTRACT

Anesthesia masks for infants are disclosed including a bowl-shaped elastic mask body which is designed to seal around the infant's face and which includes a peripheral edge for such sealing purposes and includes a central opening for connection to an anesthesia tube. The body portion of the mask includes a suction teat as part of the mask itself extending towards the infant's face, so that it can be inserted into the infant's mouth to facilitate sealing of the peripheral edge of the mask against the infant's face while the anesthesia is being administered.

7 Claims, 1 Drawing Sheet

ANESTHETIC MASK FOR INFANTS

FIELD OF THE INVENTION

The present invention relates to anesthesia masks for infants. More particularly, the present invention relates to anesthesia masks for infants which includes a central body section with a through opening for connection of an anesthesia tube to the mask. More particularly, the present invention relates to such anesthesia masks which include a bowl-shaped elastic wall projecting from the body section which is shaped to be sealed around the facial region of the child, including both the nose and mouth of the infant.

BACKGROUND OF THE INVENTION

In order to anesthetize infants, particularly babies, an anesthesia mask for covering the infant's face (i.e., nose and mouth) is often used. Thus, during administration of the anesthetic, such masks are continuously pressed against the child's face by a nurse in order to maintain such sealed contact. Such a mask is therefore often seen by the child as a threat due to perceived difficulty in breathing through the nose while utilizing the mask. This disturbs the child so that anesthetizing becomes much more difficult.

An anesthesia administering device is known from EP-A-0 085 639 which includes a test-shaped suction piece with which the child can suck and thus draw a nozzle opening for the anesthesia gas towards himself. In this case, the nozzle is formed on the outside of the teat, and positioned in front of the infant's nose. The gas can thus be partially inhaled by the child, although the majority of the gas will flow out to the surrounding air. This known device is intended to achieve a first phase of anesthetizing, and then thereafter a normal anesthesia mask can be connected and placed over the infant's face for subsequent anesthetizing (see page 4, lines 26–32; page 5, lines 1 and 2 of the EP publication).

An object of the present invention is to provide an anesthesia mask for infants which the child will happily accept so as to achieve a gradual sealing contact of the outer peripheral edge of the bowl-shaped wall of the mask against the face of the child around the nose and mouth so as to prevent leakage of anesthesia gas around the mask and to thereby obtain complete anesthesia with one single pass.

SUMMARY OF THE INVENTION

In accordance with the present invention, these and other objects have now been accomplished by the invention of an anesthesia mask for use by infants which includes a bowl-shaped elastic body portion adapted for sealingly surrounding the face of the infant around the nose and mouth and including a peripheral edge portion, with the body portion including a central opening for connection to an anesthesia tube, the body portion further including suction means unitary therewith and extending within the body portion towards the infant's face whereby insertion of the suction means into the infant's mouth facilitates sealing of the peripheral edge against the infant's face and application of the anesthetic by the infant sucking on the suction means. In a preferred embodiment, the peripheral edge portion includes an inwardly directed bead, and the suction means is teat-shaped, and preferably is completely sealed. In accordance with another embodiment of this invention, the central opening includes nipple means for connection to the anesthesia tube.

Thus, in order to achieve the objects of this invention, the anesthesia mask hereof is characterized by the fact that a test-shaped suction piece is formed unitarily with a section of the wall beneath the through opening which is to be connected to the anesthesia tube. Suction piece is thus intended to be inserted into the child's mouth in order to facilitate a gradual sealing contact of the wall's outer peripheral edge against the infant's face by means of the child sucking on the suction piece.

BRIEF DESCRIPTION OF THE DRAWINGS

A more complete understanding of the subject matter of the anesthesia mask of the present invention may be had with reference to the following detailed description, which refers to the attached drawings in which.

DETAILED DESCRIPTION

Figure 1:
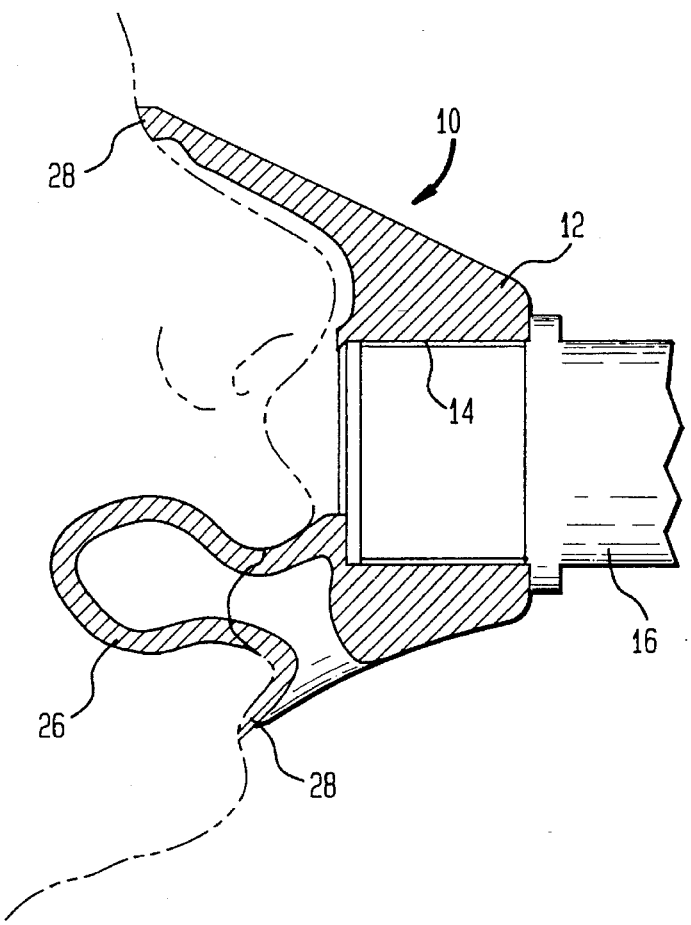
FIG. 1 is a side, partially sectional, elevational view of a suction mask according to the present invention in use.
Figure 2:
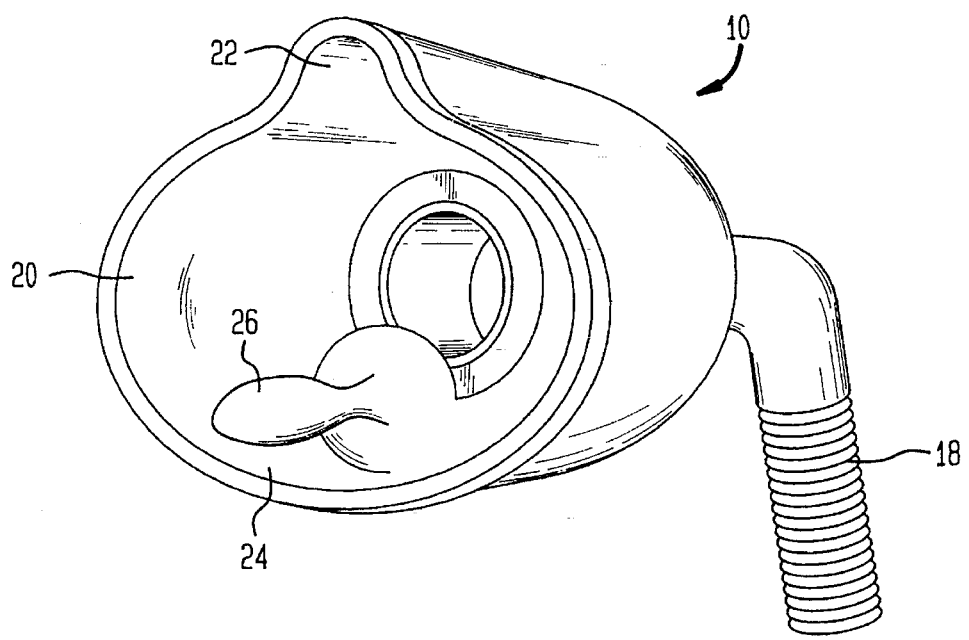
FIG. 2 is a front elevational perspective view from the inside of the mask as shown in FIG. 1.

Referring to the figures, in which like numerals refer to like portions thereof, the anesthesia mask 10 according to the present invention is preferably made from rubber or another suitable elastic material, and comprises a central body section 12 with a through-opening 14 for a connection nipple 16 which is intended to be connected to an external anesthesia gas tube 18 in order to direct a flow of gas towards the nostrils. A bowl-shaped wall 20 projects from the central section 12 and presents an upper region 32 which surrounds the child's nose, and a lower section 24 on which an inwardly projecting test-shaped suction piece 26 is formed. The suction piece is totally sealed and formed in one piece with the lower section 24 of the mask's wall and is intended to be inserted in the child's mouth.

The wall 20 has an outer peripheral edge with a bead 28 on the side of the mask facing the child. The purpose of the bead 28 is to form a sealing contact of the mask against the child's face.

Before the mask is used, a sugar solution or the like may be applied to the teat-shaped suction piece 26, whereafter the suction piece is inserted into the child's mouth so that the child can happily such on it and so that peripheral edge of the mask is then drawn into sealing contact with the face around the nose and mouth (see FIG. 1). Anesthesia gas can thereafter be administered to anesthetize the child.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

I claim:

1. An anesthesia mask for use by infants comprising:

a bowl shaped elastic body portion adapted for sealingly surrounding a face of an infant around a nose and a mouth, said body portion having a peripheral edge including an inwardly directed bead and an interior portion with a central opening for connection to an anesthesia tube; and means to facilitate sealing of said peripheral edge against the face and to substantially prevent entrance of anesthetic into the mouth from said interior portion, said means including a teat shaped suction piece independent of said central opening and unitary with the bowl shaped elastic body portion, said teat shaped suction piece having upper and lower surfaces for sealing engagement with the lips being displaced from said central opening and positioned for insertion into the mouth of the infant;

whereby as the infant sucks on said teat shaped suction piece entrance of the anesthetic into the mouth is blocked and the peripheral edge is drawn into sealing engagement with the face.

2. The anesthesia mask of claim 1, wherein said central opening includes nipple means for connection to said anesthesia tube.

3. The anesthesia mask of claim 1, wherein said teat shaped suction piece is substantially vertically displaced from said central opening.

4. The anesthesia mask of claim 3, wherein said teat shaped suction piece is situated within said bowl shaped elastic body substantially downwardly from said central opening.

5. The anesthesia mask of claim 1, wherein said peripheral edge does not extend beyond said face of the infant.

6. The anesthesia mask of claim 1, wherein upon insertion of said teat shaped suction piece into said mouth said upper surface sealingly engages an upper lip of said face of the infant.

7. The anesthesia mask of claim 6, wherein said central opening faces said nose of the infant.

* * * * *

UNITED STATES PATENT AND TRADEMARK OFFICE
CERTIFICATE OF CORRECTION

PATENT NO. : 5,462,050

DATED : October 31, 1995

INVENTOR(S) : Monika Dahlstrand

It is certified that error appears in the above-identified patent and that said Letters Patent is hereby corrected as shown below:

Column 1, line 27, "test-shaped" should read --teat-shaped--.

Column 2, line 2, "test-shaped" should read --teat-shaped--.

Column 2, line 30, "32" should read --22--.

Column 2, line 32, "test-shaped" should read --teat-shaped--.

Signed and Sealed this

Thirtieth Day of January, 1996

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,462,050
DATED : October 31, 1995
INVENTOR(S) : Monika Dahlstrand

It is certified that error appears in the above-indentified patent and that said Letters Patent is hereby corrected as shown below:

Column 2, line 43, "such" should read --suck--.

Signed and Sealed this

Second Day of April, 1996

Attest:

BRUCE LEHMAN

Attesting Officer    Commissioner of Patents and Trademarks